United States Patent [19]

Kreuzer et al.

[11] Patent Number: 4,511,728
[45] Date of Patent: Apr. 16, 1985

[54] SILANES AND COMPOSITIONS PREPARED THEREFROM

[75] Inventors: Franz-Heinrich Kreuzer, Martinsried; Gisela Glauberman, Munich; Erhard Bosch, Burghausen, all of Fed. Rep. of Germany

[73] Assignee: Consortium für Elektrochemische, Munich, Fed. Rep. of Germany

[21] Appl. No.: 454,810

[22] Filed: Dec. 30, 1982

[30] Foreign Application Priority Data

Mar. 20, 1982 [DE] Fed. Rep. of Germany ....... 3210337

[51] Int. Cl.³ .......................... C07F 7/08; C07F 7/10; C07F 7/18
[52] U.S. Cl. .................................. 556/419; 556/437; 528/34
[58] Field of Search .............................. 556/437, 419

[56] References Cited

U.S. PATENT DOCUMENTS 1,918,338  7/1933  Kaufmann .......................... 556/437
3,595,894  7/1971  Brown et al. ....................... 556/437
3,806,533  4/1974  Tessler ............................... 556/437

FOREIGN PATENT DOCUMENTS 0160684  6/1933  Switzerland ................ 556/419 UX Primary Examiner—Paul F. Shaver

[57] ABSTRACT

This invention relates to silanes of the general formula $$R_nSi(OCR_2^1COZR)_{4-n}$$

where R represents the same or different monovalent hydrocarbon radicals or substituted monovalent hydrocarbon radicals, $R^1$ is hydrogen or the same as R, Z is oxygen or the group $$\begin{array}{c} R^1 \\ | \\ -N- \end{array},$$

where $R^1$ is the same as above, n is 0 or 1 and oligomers thereof. These silanes are prepared by reacting silanes of the general formula $$R_nSiX_{4-n}$$

where R and n are the same as above and X represents the same or different hydrolyzable atoms or condensable groups other than $RCOCR_2^1CO$ groups, with alpha-hydroxycarboxylic acid esters or amides. The silanes, which have at least three condensable groups per molecule, may be mixed with a diorganopolysiloxane containing terminal condensable groups and at least one additional substance to prepare compositions which are storage-stable under anhydrous conditions, but crosslink when exposed to moisture at room temperature to form elastomers.

4 Claims, No Drawings

SILANES AND COMPOSITIONS PREPARED THEREFROM

The present invention relates to silicon compounds, particularly to silanes having at least three condensable groups per molecule and more particularly to room temperature curable organopolysiloxane compositions.

BACKGROUND OF THE INVENTION

Compositions which are stable under anhydrous conditions, but crosslink to form elastomers when exposed to moisture at room temperature are known in the art. For example, these compositions may be prepared by mixing a diorganopolysiloxane having terminal condensable groups with a silicon compound containing at least three condensable groups per molecule, and at least one additional substance. U.S. Pat. No. 4,176,112 to Cella et al, for example, describes moisture curable alkoxyorganopolysiloxanes which are prepared by combining 1, 3-dicarbonyl cyclic alkoxysilanes with silanol terminated organopolysiloxanes. The silanes described by Cella et al contain an organic radical which has a carbonyl group that is bonded to silicon via oxygen.

It is an object of the present invention to provide silanes containing at least three condensable groups per molecule. Another object of the present invention is to provide silanes which will crosslink with organopolysiloxanes containing condensable groups. Another object of the present invention is to provide a process for preparing silanes having at least three condensable groups per molecule. Still another object of the present invention is to provide an organopolysiloxane composition which is stable under anhydrous conditions. A further object of the present invention is to provide compositions containing diorganopolysiloxanes having terminal condensable groups, a silane having at least three condensable groups per molecule and an additional substance, which will crosslink within an acceptable period of time. A still further object of the present invention is to provide an organopolysiloxane composition which will crosslink at room temperature in the presence of moisture without generating odor, toxic or corrosive substances.

SUMMARY OF THE INVENTION

The foregoing objects and others which will become apparent from the foregoing description are accomplished in accordance with this invention, generally speaking, by providing silanes of the general formula $$R_nSi(OCR_2^1COZR)_{4-n}$$

where R represents the same or different monovalent hydrocarbon radicals, or substituted monovalent hydrocarbon radicals; $R^1$ is hydrogen or the same as R; Z is oxygen or the group

wherein $R^1$ is the same as above, n is 0 or 1, and oligomers thereof. These silanes are prepared by reacting silanes of the general formula $$R_nSiX_{4-n},$$

where R and n are the same as above and X represents the same or different hydrolyzable atoms or condensable groups other than the $RZOCR_2^1CO$ groups, with an alpha-hydroxycarboxylic acid ester or amide. The silanes or oligomer(s) of this invention may be mixed with diorganopolysiloxanes containing terminal condensable groups and an additional substance to form a composition which is stable under anhydrous conditions, but crosslinks when exposed to atmospheric moisture at room temperature to form organopolysiloxane elastomers.

DETAILED DESCRIPTION OF THE INVENTION

The oligomers can be prepared during the preparation of the above silanes, or from the partial hydrolysis of the silanes.

These oligomers are compounds containing at least two silicon atoms which are bonded to each other by siloxane-oxygen and contain at leas three $RZOCR_2^1CO$ groups per molecule.

Examles of hydrocarbon radicals represented by R and $R^1$ are linear or branched alkyl radicals such as the methyl, ethyl, n-propyl, isopropyl, n-butyl, sec-butyl and the 2-ethylhexyl radical; cycloalkyl radicals such as the cyclohexyl radical and methylcyclohexyl radicals; linear or branched alkenyl radicals such as the vinyl, the allyl and the methallyl radical; aryl radicals such as the phenyl radical; alkaryl radicals such as the tolyl radicals; and aralkyl radicals such as the beta-phenylethyl radical.

Examples of substituted monovalent hydrocarbon radicals represented by R and $R^1$ are halogenated hydrocarbon radicals, such as the 3,3,3-trifluoropropyl radical, chlorophenyl and bromophenyl radicals and cyanoalkyl radicals such as the beta-cyanoethyl radical.

Various $R^1$ radicals may of course be bonded to a single carbon atom, and the R radicals that are bonded to the silicon atom and to Z may also be the same or different and different $RZOCR_2^1CO$ groups may be present in a molecule.

Specific examples of silanes of this invention are those having the following formulas:

$$Si(OCH_2COO-n-C_4H_9)_4,$$

$$Si[OCH_2COOCH_2CH(C_2H_5)C_4H_9]_4,$$

$$Si(OCH_2COO-n-C_4H_9)_a[OCH_2COOCH_2CH(C_2H_5)C_4H_9]_b,$$

where a+b are each numbers whose sum is 4, $$Si[OCH(CH_3)COO-n-C_4H_9]_4, \text{ and}$$

$$CH_2=CHSi[OCH_2COOCH_2CH(C_2H_5)C_4H_9]_3.$$

An example of an oligomer of the silane of this invention is a compound having the following formula:

$$(n-C_4H_9OOCCH_2O)_3SiOSi(OCH_2COO-n-C_4H_9)_3.$$

In the preparation of the silanes of this invention, a silane of the general formula $$R_nSiX_{4-n},$$

where R and n are the same as above and X represents the same or different hydrolyzable atoms or condensable groups other than the $RZOCR^1_2CO$ groups, is reacted with an alpha-hydroxycarboxylic acid ester or amide. Examples of hydrolyzable atoms represented by X are halogen atoms, especially fluorine, chlorine, bromine or iodine atoms and hydrogen atoms.

Examples of other groups represented by X are acyloxy groups such as acetoxy groups, and amino groups in which at least one hydrogen atom can be substituted with a hydrocarbon group; alkoxy groups such as methoxy or ethoxy groups; oxime groups such as acetonoxime groups and methylethylketoxime groups as well as alkenyloxy groups, such as isopropenyl and isobutenyloxy groups.

Because of its availability, it is preferred that X be chlorine. In preparing the silanes or oligomers of this invention, silicon tetrachloride is the preferred silane.

Although only one type of silane corresponding to the general formula $R_nSiX_{4-n}$ may be used; a mixture containing at least two different silanes of the type described above may be employed.

The alpha-hydroxycarboxylic acid esters can be represented by the general formula $$ROOCR^1_2COH,$$

while alpha-hydroxycarboxylic acid amides can be represented by the general formula $$RNR^1OCR^1_2COH,$$

where R and $R^1$ are the same as above.

Specific examples of alpha-hydroxycarboxylic acid esters are glycolic acid-n-butylester, glycolic acid-2-ethylhexylester and lactic acid-n-butylester.

The silanes of this invention may be prepared from only one type of alpha-hydroxycarboxylic acid ester or alpha-hydroxycarboxylic acid amide. However, it is also possible to employ a mixture of at least two different types of alpha-hydroxycarboxylic acid esters or alpha-hydroxycarboxylic acid amides, or a mixture comprising at least one alpha-hydroxycarboxylic acid ester and at least one alpha-hydroxycarboxylic acid amide.

The reaction of silanes having the general formula $$R_nSiX_{4-n}$$

with an alpha-hydroxycarboxylic acid ester or an alpha-hydroxycarboxylic acid amide to prepare silanes of the general formula $$R_nSi(OCR^1_2COZR)_{4-n}$$

takes place in accordance with the following equation:

$$R_nSiX_{4-n} + 4-nHOCR^1_2COZR \rightarrow R_nSi(OCR^1_2COZR)_{4-n} + (4-n)XH.$$

This reaction can take place at temperatures between 0° and 250° C. with the preferred temperature being between 15° and 180° C. Also, it is preferred that it be carried out at atmospheric pressure, i.e., about 1030 mbar. However, if desired, higher or lower pressures may be used as well.

The reaction may be performed in an inert solvent such as methylene chloride, toluene or xylene, or in a mixture of such solvents.

Room temperature crosslinkable organopolysiloxane compositions may be prepared by mixing silanes having the general formula $$R_nSi(OCR^1_2COZR)_{4-n},$$

where R, $R^1$, Z and n are the same as above or oligomer(s) thereof, with diorganopolysiloxanes having terminal condensable groups and at least one other substance. The resultant compositions, which are stable under anhydrous conditions, crosslink when exposed to moisture at room temperature to form elastomers.

In preparing the compositions of this invention, it is possible to use as the diorganopolysiloxanes containing terminal condensable groups, the same diorganopolysiloxanes containing terminal condensable groups which have been or could have been used heretofore in the preparation of compositions which are storage-stable under anhydrous conditions, but which crosslink to form elastomers when exposed to moisture at room temperature. The diorganopolysiloxanes which are generally used for this purpose and which are preferred in the preparation of the compositions of this invention can be represented by the general formula:

$$HO(SiR_2O)_mSiR_2OH$$

where R is the same as above and m is an integer having a value of at least 10.

Although this is generally not indicated in formulas of this type, siloxane units other than the diorganosiloxane units ($SiR_2O$) may be present within or along the siloxane chains. Examples of such other siloxane units which are generally present only more or less as unavoidable impurities, are those of the formulas $RSiO_{3/2}$, $R_3SiO_{1/2}$ and $SiO_{4/2}$, where R is the same as above. It is preferred that the total quantity of such siloxane units other than diorganosiloxane units not exceed more than about 5 mole percent of the total siloxane units present in the diorganopolysiloxanes having terminal condensable groups. If desired, the hydroxyl groups in the preceding formula may be entirely or partially substituted with other condensable groups, such as alkoxy groups having from 1 to 4 carbon atoms.

The examples for the R groups described above in the silanes of this invention are equally applicable to the R radicals in the diorganopolysiloxanes containing terminal Si-bonded hydroxyl groups as shown in the above formula. Because of their availability, it is preferred that at least 80 percent of the number of the R radicals be methyl radicals.

The diorganopolysiloxanes having terminal condensable groups may be homopolymers or copolymers of the same or different viscosity. In the preparation of the compositions of this invention only one type of diorganopolysiloxane having terminal condensable groups, or a mixture containing two or more kinds of diorganopolysiloxanes having terminal condensable groups may be used to prepare the compositions of this invention.

The viscosity of the diorganopolysiloxanes having terminal condensable groups is preferably between 1,500 to 500,000 mPa.s at 25° C.

Silanes having the general formula $$R_nSi(OCR_2^1COZR)_{4-n}$$

or oligomers thereof or mixtures of such silanes and oligomers, may be used in the compositions of this invention in an amount of from 4 to 10 parts by weight for each 100 parts by weight of the diorganopolysiloxane containing terminal condensable groups.

Examples of other substances which may be employed in the compositions of this invention are condensation catalysts such as metal or organometallic salts of carboxylic acids. Such examples of such catalysts are lead-di-2-ethylhexoate, dibutyltin diacetate, dibutyltin dilaurate, butyltintris-(2-ethylhexoate), dibutyltin diacylate in which the acylate groups are derived from a mixture of carboxylic acids containing from 9 to 11 carbon atoms per molecule and the carboxyl group of at least 90 percent by weight of the carboxylic acids is bonded to a tertiary carbon atom (so-called "dibutyldiversatate"), stannodicaproate, stannodinaphthenate, stannodioleate, stannodibutyrate, titanium tetranaphthenate, zinc dinaphthenate zinc distearate, zinc-di-2-ethylhexoate, ferro-2-ethylhexoate, cobalt(II)-2-ethylhexoate and manganese (II)-ethylhexoate; titanium compounds other than titanium salts of carboxylic acids, such as tetra-n-butyltitanate, tetra-2-ethylhexyltitanate, tetraphenyltitanate, tetraoctadecyltitanate, tetraoctyleneglycoltitanate, tetraorganosiloxytitanate, dialkoxytitane-bisacetylacetonate, tetraisopropenoxytitane, tetra-1,2-dimethyl-1-propenoxytitane and tetra-1-methyl-1-propenoxytitane; aluminum alcoholates, such as aluminum triisopropylate; cer salts, such as ceroctoate; alkali metal salts of carboxylic acids, such as potassium acetate, sodium acetate and dilithium oxalate; amines, including aminoalkylalkoxysilanes, ammonium salts, including quaternary ammonium salts, such as n-hexylamine, tris-(2-ethylhexyl)-amine, di-2-ethylhexylamine, triisononylamine, gamma-aminopropyltriethoxysilane, compounds of the formula $$H_2N(CH_2)_2NH(CH_2)_3Si(OC_2H_5)_3,$$

dodecylammonium phosphate and benzyltriethylammonium phosphate; as well as basic liquid ion exchange resins, such as Amberlite LA-2 (a registered trademark of the Serva Company) which product is a mixture of secondary amines having linear and branched aliphatic hydrocarbon radicals having from 11 to 14 carbon atoms per radical, instead of two hydrogen atoms in the ammonia molecule.

Preferred condensation catalysts are the amines, including aminoalkoxysilanes and basic liquid ion exchange resins, as well as quaternary ammonium salts, alkali metal salts of carboxylic acids, tetraalkenyloxytitanium compounds and cer salts.

In preparing the compositions of this invention, the condensation catalyst is preferably used in an amount of from 0.01 to 10 parts by weight, and more preferably in an amount of from 0.05 to 4.0 parts by weight for each 100 parts by weight of the diorganopolysiloxane having terminal condensable groups.

Examples of other substances which may be used in preparing the compositions of this invention are solvents, such as those used in diluting the condensation catalyst. Suitable solvents are benzene, toluene, xylol or perchloroethylene. Additional substances which may be used are reinforcing inorganic fillers, nonreinforcing inorganic fillers, pigments, soluble dyes, resinous organopolysiloxanes, such as those consisting of $(CH_3)_3SiO_{1/2}$ and $SiO_{4/2}$ units, pure organic resins, such as homopolymers or copolymers of acrylonitrile, polystyrene, polyvinyl chloride or polypropylene; organic polymers, especially copolymers of styrene and n-butylacrylate, which have been polymerized in the presence of a diorganopolysiloxane containing terminal condensable groups, by means of free radicals; corrosion inhibitors, oxidation inhibitors, heat-stabilizers and antistatic agents.

Examples of reinforcing inorganic fillers, i.e., inorganic fillers having a surface area of at least 50 m$^2$/g, and pyrogenically produced silicon dioxide, silicic acid hydrogels which have been dehydrated while preserving their structure, and other types of precipitated silicon dioxide having a surface area of at least 50 m$^2$/g.

Examples of nonreinforcing inorganic fillers, i.e., inorganic fillers having a surface area of less than 50 m$^2$/g, are for example quartz, metal, diatomaceous earth, ferric oxide, zinc oxide, titanium oxide, calcium carbonate, magnesium carbonate, zinc carbonate, carbon black, mica and Neuberg chalk.

Fibrous filler materials such as asbestos or fiberglass may also be present in the compositions of this invention.

When the compositions of this invention contain inorganic fillers or pure organic polymers, then these are preferably present in an amount up to about 100 percent by weight and more preferably in an amount of from 5 to 30 percent by weight, based on the weight of the diorganopolysiloxane having terminal condensable groups.

Other examples of substances which may be used in the compositions of this invention are fungicides; agents for improving their heat conductivity, such as boron nitride; agents which serve to impart fire resistance, for example, antimony trioxide and chlorinated paraffins; agents for improving the adhesion of the finished elastomers to the substrates on which they are formed, for example, gamma-glycidyloxypropyltriethoxysilane; agents which delay skin formation, such as silanes containing an SiC-bonded mercaptoalkyl radical; emollients, such as dimethylpolysiloxanes or phosphoric acid esters which are fluid at room temperature and which are end-blocked by trimethylsiloxy groups; ultraviolet absorbers and cell-generating agents such as azodicarbonamide.

In preparing the compositions of this invention, all constitutents may be mixed together in any sequence. It is preferred that mixing take place at room temperature and preferably under anhydrous conditions. If desired, mixing can also take place at elevated temperatures, for example, at temperatures of from about 35° to 150° C.

The moisture normally present in the air is sufficient to bring about the crosslinking of the compositions of this invention. However, crosslinking may take place at temperatures higher or lower than room temperature, for example, at temperatures of from about −5° C. up to about +10° C. Crosslinking can also be performed at water concentrations which exceed the normal moisture content of the atmosphere.

The compositions of this invention may be used for sealing fissures and similar cavities, for example, in buildings, land, water and airborne vehicles, or they may be used as adhesives and sealants, for example in windows or in manufacturing aquariums or showcases, as well as in preparing protective coatings, including those applied to surfaces exposed to fresh or salt water. Also, they may be used as anti-slip coatings, or in the preparation of insulating coatings for electrical or electronic devices which could heretofore be prepared from elastomers which harden at room temperature.

The following examples are for purposes of illustration and are not to be construed as being limited to the following embodiments.

EXAMPLE 1

To a 4-necked flask equipped with a stirrer, a dropping funnel, a gas conduit, a reflux condenser and containing 680 g of silicon tetrachloride are added dropwise with constant stirring over a period of 1 hour, 2114 g of glycolic acid-n-butylester. About 15 minutes after the addition is complete, the contents of the flask are heated to 100° C. and nitrogen is passed through the liquid in the flask in order to remove the hydrogen chloride.

The resultant product consists of 2155 g of a light yellow liquid, which consists essentially of a silane having the formula:

$$Si(OCH_2COO—n—C_4H_9)_4.$$

EXAMPLE 2

The procedure of Example (1) is repeated, except that the reaction is heated at 40° C. in the presence of 2.5 liters of methylene chloride. After the methylenechloride has been distilled off, a crystaline substance having a melting point of about 30° C. is obtained. The NMR spectrum of this substance when compared with the NMR spectrum of the liquid material obtained in Example (1), shows that the crystalline substance of this example contains fewer impurities.

EXAMPLE 3

About 680 g of silicon tetrachloride in 2.5 liters of toluene are added to a 4-necked flask equipped with a stirrer, a dropping funnel, a gas conduit and a reflux condenser and then 700 g of a mixture consisting of 1902 g of glycolic acid-n-butylester and 212 g of glycolic acid-2-ethylhexylester is added dropwise at 20° C. The contents of the flask are subsequently heated at 110° C. and while stirring, the remainder of the glycolic acid ester mixture is added dropwise to the mixture in the flask. A stream of nitrogen which has been heated to 110° C. is then passed through the liquid in the flask in order to remove the hydrogen chloride and the methylene chloride is distilled off. The resulting liquid consists essentially of a silane having the formula:

$$Si(OCH_2COO—n—C_4H_9)_a[OCH_2COOCH_2CH(C_2H_5)C_4H_9]_b$$

where a+b=4 and whose purity is comparable to that of the crystalline substance obtained in Example (2).

EXAMPLE 4

The procedure described in Example (1) is repeated, except that the same molar quantity of glycolic acid-2-ethylhexylester is substituted for the 2114 g of glycolic acid-n-butylester. The product is a liquid which consists essentially of a silane having the formula:

$$Si[OCH_2COOCH_2CH(C_2H_5)C_4H_9]_4.$$

EXAMPLE 5

The procedure described in Example (4) is repeated, except that the same molar quantity of vinyltrichlorosilane is substituted for the 680 g of silicon tetrachloride.

The product is a liquid which corresponds substantially to a silane of the formula:

$$CH_2=CHSi[OCH_2COOCH_2(C_2H_5)C_4H_9]_3.$$

EXAMPLE 6

The procedure described in Example (1) is repeated, except that the same molar quantity of lactic acid-n-butylester is substituted for the 2114 g of glycolic acid-n-butylester. The product is a liquid which corresponds essentially to a silane of the formula:

$$Si[OCH(CH_3)COO—n—C_4H_9]_4.$$

EXAMPLE 7

About 95 g of a dimethylpolysiloxane containing terminal Si-bonded hydroxyl groups and having a viscosity of 20,000 mPa.s at 25° C. are mixed with 5 g of the silane prepared in accordance with Example (1) and 0.1 g of basic liquid ion exchange resin (Amberlite LA-2—available from the Serva Company). The resultant composition is storage-stable under anhydrous conditions, but when exposed to moisture at room temperature forms a skin in from 5 to 10 minutes immediately after its preparation. When the composition is stored for 30 days at room temperature or at 80° C. under anhydrous conditions and then exposed to moisture, it forms a skin in from 5 to 10 minutes.

EXAMPLE 8

About 83 g of a dimethylpolysiloxane containing terminal Si-bonded hydroxyl groups and having a viscosity of 80,000 mPa.s at 25° C., are mixed with 7 g of pyrogenically produced silicon dioxide having a surface area of about 300 m²/g, 10 g of the silane prepared in accordance with Example (4) and 0.1 g of basic liquid ion exchange resin (Amberlite LA-2). The resultant composition is slump-free, i.e., it does not migrate from vertical or inclined surfaces prior to crosslinking and is storage-stable under anhydrous conditions, but when exposed to moisture at room temperature forms a skin in about 5 minutes immediately after its preparation. When the composition is stored for 30 days at room temperature or at 80° C. under anhydrous conditions and then exposed to moisture, it forms a skin in about 5 minutes.

EXAMPLE 9

The procedure described in Example (7) is repeated, except that 5 g of the silane prepared in accordance with Example (5) are substituted for 5 g of the silane of Example (1). The resultant composition is storage-stable under anhydrous conditions, but when exposed to moisture forms a skin in from 25 to 30 minutes at room temperature immediately after its preparation. When the composition is stored for 30 days under anhydrous conditions either at room temperature or at 80° C. and then exposed to moisture, it forms a skin in from 25 to 30 minutes.

EXAMPLE 10

The procedure described in Example (7) is repeated, except that 5 l g of the silane prepared in accordance with Example (6) are substituted for 5 g of the silane of Example (1). The resultant composition is storage-stable under anhydrous conditions, but when exposed to moisture forms a skin in from 10 to 15 minutes at room temperature immediately after its preparation. When the composition is stored for 48 days either at room temperature or at 80° C. under anhydrous conditions and then exposed to moisture, it forms a skin in from 10 to 15 minutes.

What is claimed is:

1. Silanes of the formula $R_nSi(OCR_2^1COZR)_{4-n}$ and oligomers thereof; wherein R is selected from the group consisting of monovalent hydrocarbon radicals and substituted monovalent hydrocarbon radicals, $R^1$ is selected from the group consisting of hydrogen and R, Z is an $$\begin{array}{c} R^1 \\ | \\ -N- \end{array}$$

group, where $R^{1\ 1\ is\ the\ same\ as\ above\ and\ n\ is}$ 0 or 1.

2. A process for preparing silanes of the formula $R_nSi(OCR_2^1COZR)_{4-n}$ and oligomers thereof which comprises reacting a silane of the general formula $$R_nSiX_{4-n},$$

with an alpha-hydroxycarboxylic acid amide, wherein R is selected from the group consisting of monovalent hydrocarbon radicals and substituted monovalent hydrocarbon radicals, $R^1$ is selected from the group consisting of hydrogen and R, Z is an $$\begin{array}{c} R^1 \\ | \\ -N- \end{array}$$

group, where $R^1$ is the same as above, X is selected from the group consisting of hydrolyzable atoms and condensable groups other than $RCOCR_2^1CO$ groups and n is 0 or 1.

3. The process of claim 2, wherein the silane having the formula $R_nSiX_{4-n}$ is silicon tetrachloride.

4. The process of claim 2, wherein the reaction is carried out in an inert solvent.

* * * * *

UNITED STATES PATENT AND TRADEMARK OFFICE
CERTIFICATE OF CORRECTION

PATENT NO. : 4,511,728
DATED : April 16, 1985
INVENTOR(S) : Kreuzer, et al

It is certified that error appears in the above-identified patent and that said Letters Patent is hereby corrected as shown below:

On the title page, under "Assignee:", after "Consortium für Elektrochemische," insert --Industrie GmbH--.

Signed and Sealed this

Seventeenth Day of September 1985

[SEAL]

*Attest:*

DONALD J. QUIGG

*Attesting Officer*

*Commissioner of Patents and Trademarks—Designate*